United States Patent
Das et al.

(10) Patent No.: US 10,918,584 B2
(45) Date of Patent: Feb. 16, 2021

(54) ORAL CARE COMPOSITIONS AND METHODS FOR THE SAME

(71) Applicant: COLGATE-PALMOLIVE COMPANY, New York, NY (US)

(72) Inventors: Aradhana Das, Raritan, NJ (US); Hongwei Shen, Holmdel, NJ (US); Yun Xu, Langhorne, PA (US); Eric Simon, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 33 days.

(21) Appl. No.: 16/232,839

(22) Filed: Dec. 26, 2018

(65) Prior Publication Data

US 2020/0206113 A1    Jul. 2, 2020

(51) Int. Cl.
| | |
|---|---|
| *A61K 8/42* | (2006.01) |
| *A61K 8/60* | (2006.01) |
| *A61K 8/44* | (2006.01) |
| *A61Q 11/00* | (2006.01) |
| *A61K 8/19* | (2006.01) |

(52) U.S. Cl.
CPC .......... *A61K 8/42* (2013.01); *A61K 8/19* (2013.01); *A61K 8/44* (2013.01); *A61K 8/604* (2013.01); *A61Q 11/00* (2013.01); *A61K 2800/28* (2013.01); *A61K 2800/30* (2013.01); *A61K 2800/596* (2013.01)

(58) Field of Classification Search
None
See application file for complete search history.

(56) References Cited

U.S. PATENT DOCUMENTS

| 8,980,233 | B2 | 3/2015 | Swett et al. |
|---|---|---|---|
| 2005/0049160 | A1 | 3/2005 | Szewczyk et al. |
| 2009/0202451 | A1 | 8/2009 | Prencipe et al. |
| 2010/0041577 | A1 | 2/2010 | Tippetts et al. |
| 2011/0206629 | A1 | 8/2011 | Molenda et al. |
| 2012/0009127 | A1 | 1/2012 | Dasgupta et al. |
| 2012/0171146 | A1 | 7/2012 | Hoffmann et al. |
| 2014/0112879 | A1 | 4/2014 | Molenda et al. |
| 2014/0161743 | A1 | 6/2014 | Swett et al. |
| 2014/0348759 | A1 | 11/2014 | Hawkins et al. |
| 2015/0125415 | A1 | 5/2015 | Klug et al. |
| 2015/0164755 | A1 | 6/2015 | Klug et al. |
| 2015/0164756 | A1 | 6/2015 | Klug et al. |
| 2017/0002297 | A1 | 1/2017 | Klug et al. |
| 2017/0360672 | A1 | 12/2017 | Maka et al. |
| 2017/0367939 | A1 | 12/2017 | Thomson et al. |
| 2019/0343737 | A1* | 11/2019 | Baig ................... A61K 8/20 |

FOREIGN PATENT DOCUMENTS

EP    2855651 B1    5/2013

OTHER PUBLICATIONS

Database WPI Week 201414 Thomson Scientific, London, GB; AN 2014-B17215 XP002789995, Guangzhou Weimeizi Ind. Co. Ltd. (2013).

\* cited by examiner

*Primary Examiner* — Nannette Holloman

(57) ABSTRACT

An oral care composition and methods for the same are disclosed herein. The oral care composition may include an orally acceptable vehicle, an anionic surfactant, and a nonionic surfactant. The anionic surfactant may include a C6-C18 fatty acid glutamate or a salt thereof, and the nonionic surfactant may include a C6-C18 alkyl polyglucoside. A weight ratio of the nonionic surfactant to the anionic surfactant may be from about 0.25:1 to about 9:1, or from about 1.8:1 to about 2.2:1.

17 Claims, No Drawings

ORAL CARE COMPOSITIONS AND METHODS FOR THE SAME

BACKGROUND

Dentin or dentinal hypersensitivity is a common clinical condition associated with exposed dentin surfaces of the teeth. Dentin contains a large number of pores or dentin tubules that extend from outer surfaces of the teeth to the nerves within the teeth. As such, exposure of the dentin often leads to increased sensitivity of the teeth to external stimuli (e.g., temperature, pressure, etc.). In view of the foregoing, conventional oral care products or compositions thereof may often attempt to numb the nerve or incorporate filling or blocking agents to ameliorate the sensitivity of the teeth. For example, conventional oral care compositions, such as Colgate Sensitive Pro-Relief®, often include arginine and calcium carbonate as blocking agents to occlude the dentin and reduce sensitivity.

While conventional oral care compositions have proven to be effective in reducing sensitivity, the active ingredients (e.g., arginine, calcium carbonate, etc.) may often react with one or more foaming agents of the oral care compositions to thereby reduce the ability of the oral care compositions to generate foam. For example, conventional oral care compositions primarily utilize anionic surfactants, such as sodium lauryl sulfate, as the primary foaming agent. The anionic surfactants, however, react with the cationically charged arginine and the calcium cations provided by the calcium carbonate to produce insoluble salts, thereby reducing the availability of the foaming agent and the foaming capacity thereof. Further, consumer studies and surveys have shown that there is a desire to use oral care compositions that do not contain any sodium lauryl sulfate, as some consumers experience relatively greater sensitivity to this ingredient.

What is needed, then, are improved desensitizing oral care compositions and methods for the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition including an orally acceptable vehicle, an anionic surfactant, and a nonionic surfactant. The anionic surfactant may include a C6-C18 fatty acid glutamate or a salt thereof. The nonionic surfactant may include a C6-C18 alkyl polyglucoside. In at least one example, a weight ratio of the nonionic surfactant to the anionic surfactant may be from about 0.25:1 to about 9:1. In another example, the weight ratio of the nonionic surfactant to the anionic surfactant may be from about 1.8:1 to about 2.2:1.

In at least one implementation, the C6-C18 fatty acid glutamate or the salt thereof may include a cocoyl glutamate salt. In at least one example, the cocoyl glutamate salt is a sodium cocoyl glutamate.

In at least one implementation, the C6-C18 alkyl polyglucoside may include a short chain alkyl polyglucoside. In at least one example, the short chain alkyl polyglucoside may include a C6-C10 alkyl polyglucoside.

In at least one implementation, the C6-C18 alkyl polyglucoside may include a long chain alkyl polyglucoside. In at least one example, the long chain alkyl polyglucoside may include a C11-C18 alkyl polyglucoside.

In at least one implementation, the oral care composition may further include an amino acid. In at least one example, the amino acid may include one or more of arginine, lysine, citrulline, ornithine, creatine, histidine, diaminobutanoic acid, diaminoproprionic acid, salts thereof, or combinations thereof. In at least one example, the amino acid may include arginine. The arginine may be provided by arginine bicarbonate. The arginine may also be provided by an arginine bicarbonate solution.

In at least one implementation, the oral care composition may further include an abrasive. The abrasive may include one or more of sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, calcium carbonate, magnesium carbonate, hydrated alumina, silica, zirconium silicate, aluminum silicate, calcined aluminum silicate, polymethyl methacrylate, or combinations thereof. In one example, the abrasive may include calcium carbonate. In another example, the calcium carbonate may include natural calcium carbonate or precipitated calcium carbonate.

In at least one implementation, the oral care composition may be free or substantially free of alkyl sulfate salts. In one example, the oral care composition may be free or substantially free of sodium lauryl sulfate.

In at least one implementation, the oral care composition may be a toothpaste.

The foregoing and/or other aspects and utilities embodied in the present disclosure may be achieved by providing a method for preparing any one or more of the oral care composition disclosed herein. The method may include contacting the orally acceptable vehicle, the anionic surfactant, and the nonionic surfactant with one another.

The foregoing and/or other aspects and utilities embodied in the present disclosure may be achieved by providing a method for treating dentinal hypersensitivity in a human. The method may include contacting any one or more of the oral care composition disclosed herein with surfaces of teeth of the human.

In at least one implementation, the method may include contacting the oral care composition with surfaces of the teeth of the human at least once a day, optionally, twice a day.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that oral care compositions including the combination of a glutamate surfactant, particularly, sodium cocoyl glutamate, and an alkyl polyglucoside surfactant exhibit synergistic or more than additive foaming as compared to each of the surfactants alone. Without being bound by theory, it is believed that the nonionic structure of the glucoside surfactant and the negatively charged structure of the glutamate surfactant may contribute to the synergistic results. Particularly, it is believed that the nonionic structure of the glucoside surfactant and the negatively charged structure of the glutamate surfactant prevents interactions between them, thereby increasing the foaming in the toothpaste formulation.

The present inventors have also surprisingly and unexpectedly discovered that relatively greater amounts of the nonionic polyglucoside surfactant to the anionic glutamate surfactant surprisingly and unexpectedly produced more foam as compared to toothpaste compositions including relatively greater amounts of the anionic glutamate surfactant. Accordingly, it was surprisingly and unexpectedly discovered that increased amounts or ratios of the nonionic surfactant relative to the anionic surfactant provided improved foaming.

Compositions

Compositions disclosed herein may be or include an oral care product or an oral care composition thereof. For example, the compositions disclosed herein may be an oral care product including an oral care composition or the oral care composition thereof. In at least one implementation, the compositions disclosed herein may be or include oral care compositions including an orally acceptable vehicle or carrier and one or more surfactants or foaming agents capable of or configured to provide relatively greater foam production as compared to conventional oral care compositions. For example, compositions disclosed herein may be or include oral care compositions, such as toothpaste compositions for sensitive teeth, that include an orally acceptable vehicle or carrier and one or more surfactants capable of or configured to provide relatively greater foam production as compared to conventional oral care compositions, which utilize conventional cationically charged surfactants, such as sodium lauryl sulfate (SLS). As further described herein, the one or more surfactants may include an anionic surfactant and a nonionic surfactant, where the anionic surfactant may be or include a C6-C18 fatty acid glutamate or a salt thereof, and where the nonionic surfactant may be or include a C6-C18 alkyl polyglucoside, and where a weight ratio of the nonionic surfactant to the anionic surfactant is from about 0.25:1 to about 9:1. In another implementation, the oral care composition may include an orally acceptable vehicle or carrier, the anionic surfactant, the nonionic surfactant, one or more amino acids (e.g., arginine), and one or more abrasives (e.g., calcium carbonate).

Illustrative oral care products or compositions of the present disclosure may be or include, but are not limited to, a toothpaste (dentifrice), a prophylactic paste, a tooth powder, or a tooth gel (e.g., a whitening gel). In an exemplary implementation, the oral care composition disclosed herein may be a dentifrice or toothpaste. For example, the oral care composition disclosed herein may be a toothpaste for treating teeth sensitivity or dentinal hypersensitivity.

The oral care product or the oral care composition thereof may be a single phase oral care product or a single phase oral care composition. For example, all the components of the oral care product or the oral care composition thereof may be maintained together with one another in a single phase and/or vessel. For example, all the components of the oral care product or the oral care composition thereof may be maintained in a single phase, such as a single homogenous phase. In another implementation, the oral care product or the oral care composition thereof may be a multi-phase oral care product or a multi-phase oral care composition.

The oral care product or the oral care composition thereof prior to use may have a "low water content". As used herein, "low water content" may refer to a composition that contains water in an amount greater than about 5 weight % and less than about 15 weight %, less than about 13 weight %, less than about 10 weight %, or less than about 7 weight %, based on a total weight of the oral care composition. In another implementation, the oral care product or the oral care composition thereof prior to use may be an anhydrous formulation or an anhydrous composition. For example, the oral care composition prior to use may be anhydrous, free, or substantially free of water. As used herein, "free of water" or "substantially free of water" may refer to a composition that contains water in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on the total weight of the oral care composition.

Amino Acid

The oral care composition may include one or more amino acids. The one or more amino acids of the oral care composition may be in free or salt form. Illustrative amino acids that may be utilized in the oral care composition may include, but are not limited to, arginine, lysine, citrulline, ornithine, creatine, histidine, diaminobutanoic acid, diaminoproprionic acid, salts thereof and/or combinations thereof. The amino acids of the oral care composition may generally be present in the L-form or L-configuration. The amino acids may be provided as a salt of a di- or tri-peptide including the amino acid. In at least one implementation, at least a portion of the amino acid present in the oral care composition is in the salt form. In a preferred implementation, the oral care composition includes at least arginine (e.g., L-arginine) or a source of arginine. The arginine may be provided as free arginine or a salt thereof. For example, the arginine may be provided as arginine phosphate, arginine hydrochloride, arginine sulfate, arginine bicarbonate, or the like, and mixtures or combinations thereof. The one or more amino acids may be provided as a solution or a solid. For example, the one or more amino acids may be provided as an aqueous solution. In a preferred implementation, the one or more amino acids include or is provided by an arginine bicarbonate solution.

The amount or concentration of the one or more amino acids present in the oral care composition may vary widely. In at least one implementation, the amount or concentration of the one or more amino acids may be from greater than 0 weight % to about 20 weight %, based on the total weight of the oral care composition. For example, the amount of one or more amino acids present in the oral care composition may be from greater than 0 weight %, about 2 weight %, about 4 weight %, about 6 weight %, about 8 weight %, or about 10 weight % to about 12 weight %, about 14 weight %, about 16 weight %, about 18 weight %, or about 20 weight %, based on the total weight of the oral care composition. In another example, the amount of one or more amino acids present in the oral care composition may be from greater than 0 weight % to about 20 weight %, about 4 weight % to about 12 weight %, about 6 weight % to about 10 weight %, or about 8 weight %, based on the total weight of the oral care composition. In a preferred embodiment, the oral care composition includes from about 6 weight % to about 10 weight % or about 8 weight %, based on a total weight of the oral care composition, and the amino acid may be provided by a solution. For example, the amino acid may be provided by an about 40% solution of the one or more amino acids, such as arginine.

Abrasive or Abrasive System

The oral care compositions may include one or more abrasives or an abrasive system including one or more abrasives. As used herein, the term "abrasive" may also refer to materials commonly referred to as "polishing agents". Any orally acceptable abrasive may be used, but preferably, type, fineness (particle size), and amount of the abrasive may be selected such that the tooth enamel is not excessively abraded in normal use of the oral care composition.

The one or more abrasives may have a particle size or D50 of less than or equal to about 10 µm, less than or equal to about 8 µm, less than or equal to about 5 µm, or less than or equal to about 3 µm. The one or more abrasives may have a particle size or D50 of greater than or equal to about 0.01 µm, greater than or equal to about 0.05 µm, greater than or equal to about 0.1 µm, greater than or equal to about 0.5 µm, or greater than or equal to about 1 µm. Illustrative abrasives may include, but are not limited to, metaphosphate compounds, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, calcium carbonate (e.g., precipitated calcium carbonate and/or natural calcium carbonate), magnesium carbonate, hydrated alumina, silica, zirconium silicate, aluminum silicate including calcined aluminum silicate, polymethyl methacrylate, or the like, or mixtures and combinations thereof.

In a preferred implementation, the oral care composition includes at least calcium carbonate as an abrasive. In at least one implementation, precipitated calcium carbonate may be preferred over natural calcium carbonate. While not intending to be bound by theory, it is believed that natural calcium carbonate has relatively greater crystallinity or a relatively more crystalline structure as compared to precipitated calcium carbonate, thereby making the calcium carbonate very hard. Conversely, precipitated calcium carbonate is relatively more amorphous and more friable or easily crumbled. As such, the precipitated calcium carbonate has a relatively lower abrasivity as compared to the natural calcium carbonate, while maintaining adequate cleaning power.

The one or more of the abrasives in the abrasive system may have a pellicle cleaning ratio (PCR) greater than or equal to 80, greater than or equal to 82, greater than or equal to 84, greater than or equal to 86, greater than or equal to 88, greater than or equal to 90, greater than or equal to 92, greater than or equal to 94, greater than or equal to 96, greater than or equal to 98, greater than or equal to 100, greater than or equal to 102, greater than or equal to 104, greater than or equal to 106, greater than or equal to 108, greater than or equal to 110, greater than or equal to 112, or greater.

The amount or concentration of the one or more abrasives present in the oral care composition may vary widely. In at least one implementation, the amount or concentration of the abrasives may be from greater than 0 weight % to about 60 weight %, based on a total weight of the oral care composition. For example, the amount of the abrasives present in the oral care composition may be from greater than 0 weight %, about 2 weight %, about 4 weight %, about 6 weight %, about 8 weight %, about 10 weight %, about 12 weight %, about 14 weight %, about 16 weight %, about 18 weight %, or about 19 weight % to about 21 weight %, about 22 weight %, about 24 weight %, about 26 weight %, about 28 weight %, about 30 weight %, about 32 weight %, about 34 weight %, about 36 weight %, about 38 weight %, or about 40 weight %. In another example, the amount of the abrasives present in the oral care composition may be from greater than 0 weight % to about 40 weight %, about 2 weight % to about 38 weight %, about 4 weight % to about 36 weight %, about 6 weight % to about 34 weight %, about 8 weight % to about 32 weight %, about 10 weight % to about 30 weight %, about 12 weight % to about 28 weight %, about 14 weight % to about 26 weight %, about 16 weight % to about 24 weight %, about 18 weight % to about 22 weight %, or about 19 weight % to about 21 weight %. In a preferred implementation, the amount of the abrasives present in the oral care composition may be from about 25 weight % to about 45 weight %, preferably about 30 weight % to about 40 weight %, or more preferably about 35 weight %, based on a total weight of the oral care composition.

Surfactant(s) or Foaming System

The oral care composition may include one or more surfactants or foaming agents capable of or configured to provide relatively greater foam production as compared to conventional oral care compositions. The one or more surfactants or foaming agents may be or include, but are not limited to, one or more amino acid-based surfactants, one or more anionic surfactants, one or more cationic surfactants, one or more zwitterionic surfactants, one or more nonionic surfactants, or combinations and mixtures thereof.

Illustrative amino acid surfactants may be or include glutamate surfactants, alanine surfactants, aspartate surfactants, or the like, or any mixture or combination thereof. Illustrative glutamate surfactants may be represented by formula (1):

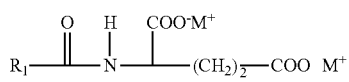

(1)

where $R_1$ may be a saturated or unsaturated, straight or branched alkyl chain with 6 to 18 carbon atoms, and more preferably 8 to 14 carbon atoms, and $M^+$ may be independent from each other H, sodium or potassium. Illustrative glutamate surfactants may be or include, but are not limited to, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, sodium lauroyl glutamate, or the like, or combinations or mixtures thereof. In at least one implementation, the anionic surfactant may be or include one or more C6-C18 fatty acid glutamate salts or amino acid surfactants, such as a cocoyl glutamate salt, particularly sodium cocoyl glutamate.

Illustrative anionic surfactants may be or include, but are not limited to, one or more C6-C18 fatty acid glutamate salts, water-soluble salts of C8-20 alkyl sulfates, sulfonated monoglycerides of C8-20 fatty acids, sarcosinates, taurates, sodium lauryl sulfate, sodium cocoyl monoglyceride sulfonate, sodium lauryl sarcosinate, sodium lauryl isethionate, sodium laureth carboxylate, sodium lauroyl methyl taurate, sodium dodecyl benzenesulfonate, water-soluble salts of higher fatty acid monoglyceride monosulfates, such as the sodium salt of the monosulfated monoglyceride of hydrogenated coconut oil fatty acids such as a sodium N-methyl-N-alkyl taurate, sodium N-methyl-N-cocoyl taurate or sodium methyl cocoyl taurate, sodium cocoyl methyl taurate, sodium lauroyl methyl taurate, sodium cocomoglyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g. 2, 3 or 4, and X is Na, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide), sodium lauryl sarcosinate, or the like, or any mixture or combination thereof. As used herein, "higher alkyl" may refer to a $C_6$-$C_{30}$ alkyl. In at least one implementation, the anionic surfactant may include one or more C6-C18 fatty acid glutamate salts or amino acid surfactants, such as a cocoyl glutamate salt, particularly sodium cocoyl glutamate.

In at least one implementation, anionic surfactants utilized in the oral care composition does not include one or more alkyl sulfate salts, such as sodium lauryl sulfate. For example, as further described herein, the oral care composition may be free or substantially free of alkyl sulfate salts, such as sodium lauryl sulfate. As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

The amphoteric and zwitterionic surfactants may be or include, but are not limited to, derivatives of $C_{8-20}$ aliphatic secondary and tertiary amines having an anionic group such as carboxylate, sulfate, sulfonate, phosphate or phosphonate. Illustrative amphoteric and zwitterionic surfactants may include, but are not limited to, sultaines and betaines, such as cocamidopropyl betaine (CAPB), derivatives of aliphatic secondary and tertiary amines in which the aliphatic radical can be a straight or branched chain and wherein one of the aliphatic substituents contains about 8-18 carbon atoms and one contains an anionic water-solubilizing group, such as carboxylate, sulfonate, sulfate, phosphate or phosphonate, or the like, and combinations thereof.

In an exemplary implementation, illustrative nonionic surfactants may be or include, but are not limited to, one or more alkyl polyglucosides, such as one or more C6-C18 alkyl polyglucosides, or the like. The C6-C18 alkyl polyglucosides may include one or more short chain alkyl polyglucosides, one or more long chain alkyl polyglucosides, or any combination thereof. As used herein, the term or expression "short chain alkyl polyglucosides" may refer to alkyl polyglucosides having a chain length of from about 6 to about 10 carbon atoms. As used herein, the term or expression "long chain alkyl polyglucosides" may refer to alkyl polyglucosides having a chain length of from about 11 to about 18 carbon atoms. It should be appreciated that the alkyl polyglucosides may include a hydrophobic fatty alcohol portion and a hydrophilic glucoside portion. In a preferred implementation, the nonionic surfactants include at least a short chain alkyl polyglucoside, such as a C6-C10 alkyl polyglucoside or a C8-C10 alkyl polyglucoside (CAS 68515-73-1), which is commercially available as APG 810. In at least one implementation, the oral care composition is free or substantially free of long chain alkyl polyglucosides.

Additional illustrative nonionic surfactants may be or include, but are not limited to, one or more of octoxynol (e.g., Macrogol tetramethylbutylphenyl ether, octylphenoxy polyethoxyethanol, or polyoxyethylene octylphenyl ether), such as octoxynol 1, 3, 5, 8, 9, 10, 12, 13, 16, 30, 40, 70, wherein the number indicates the number of repeating oxyethylene units, or other octoxynols that include different numbers of repeating units of oxyethylene in the side chain, sorbitan esters (e.g., sorbitan monooleate and sorbitan monostearate, etc.) commonly known by their trade names SPAN® 80 and SPAN® 60), polysorbates (e.g., polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of TWEEN® 80, TWEEN® 60, Tween® 20), poloxamers (synthetic block polymers of ethylene oxide and propylene oxide, such as those commonly known by their trade names of PLURONIC®; e.g., PLURONIC® F127 or PLURONIC® F108), or poloxamines (synthetic block polymers of ethylene oxide and propylene oxide attached to ethylene diamine, such as those commonly known by their trade names of TETRONIC®; e.g., TETRONIC® 1508 or TETRONIC® 908, etc.), other nonionic surfactants such as BRIJ® (polyoxyethylene alkyl ether having a formula of $CH_3—(CH_2)_{10-16}—(O—C_2H_4)_{1-25}—OH$), MYRJ® (stearic acid esterified with polyoxyethylene having 40-100 repeating oxyethylene units), long chain fatty alcohols (e.g., oleyl alcohol, stearyl alcohol, myristyl alcohol, docosahexaenoyl alcohol, etc.) with carbon chains having about 12 or more carbon atoms (e.g., such as from about 12 to about 24 carbon atoms), or the like, or any mixture or combination thereof. Additional nonionic surfactants may be or include, but are not limited to, polyethylene oxide condensates of alkyl phenols, products derived from the condensation of ethylene oxide with the reaction product of propylene oxide and ethylenediamine, ethylene oxide condensates of aliphatic alcohols, long chain tertiary amine oxides, long chain tertiary phosphine oxides, long chain dialkyl sulfoxides, or the like, or combinations thereof. In at least one implementation, the nonionic surfactants may be broadly defined as compounds produced by the condensation of alkylene oxide groups (hydrophilic in nature) with an organic hydrophobic compound, which may be aliphatic or alkylaromatic in nature.

In at least one implementation, the oral care composition may be free or substantially free of one or more surfactants capable of or configured to react with one or more cationic or cationically charged ingredients/components of the oral care composition to form insoluble salts. For example, the oral care composition may be free or substantially free of one or more surfactants capable of or configured to react with one or more cationic or cationically charged amino acids, such as arginine. In another implementation, the oral care composition may be free or substantially free of one or more surfactants capable of or configured to react with one or more cations provided or released by one or more ingredients/components of the oral care composition. For example, the oral care composition may be free or substantially free of one or more surfactants capable of or configured to react with one or more cations provided by one or more salts (e.g., inorganic salts) contained therein. For example, the oral care composition may be free or substantially free of one or more surfactants capable of or configured to react with one or more calcium ions provided by one or more abrasives of the oral care composition, such as calcium carbonate, or the like.

As discussed above, in at least one exemplary implementation, the oral care composition may be free or substantially free of sodium lauryl sulfate or similar anionic surfactants. It should be appreciated that sodium lauryl sulfate and/or anionic surfactants similar thereto may at least partially react with cationically charged species, such as partially cationically charged arginine and/or cations, such as calcium ions from calcium carbonate, to form inorganic salts. It should further be appreciated that the reaction of sodium lauryl sulfate and/or anionic surfactants similar thereto may reduce the availability and/or foaming capacity of the sodium lauryl sulfate and/or anionic surfactants similar thereto; and thus, reduce the foaming of the oral care composition. As such, in at least one exemplary implementation, the oral care composition may be free or substantially free of sodium lauryl sulfate or similar anionic surfactants.

The amount of any one or more of the surfactants or foaming agents present in the oral care composition or a component (e.g., hydrophilic or hydrophobic phases) thereof may vary widely. In at least one implementation, the amount of any one or more of the surfactants or foaming agents present in the oral care composition or the component thereof may be greater than 0.0 weight % or 0.1 weight % and less than or equal to 10.0 weight %, based on a total weight of the oral care composition or the component thereof. For example, the amount of any one or more of the surfactants or foaming agents present in the oral care composition or the component thereof may be from greater than 0 weight %, about 0.1 weight %, about 0.5 weight %, about 1 weight %, about 1.5 weight %, about 2 weight %, or about 2.5 weight % to about 3 weight %, about 3.5 weight %, about 4 weight %, about 4.5 weight %, about 5 weight %, about 8 weight %, or about 10 weight %, based on a total weight of the oral care composition or the component thereof. In another example, the amount of the surfactant present in the oral care composition or the component thereof may be from about 0.5 weight % to about 5 weight %, about 1 weight % to about 4.5 weight %, about 1.5 weight % to about 4 weight %, about 2 weight % to about 3.5 weight %, or about 2.5 weight % to about 3 weight %, based on a total weight of the oral care composition or the component thereof. In an exemplary implementation, each of the one or more of the surfactants or foaming agents may, separately and independently, be present in the oral care composition or the component thereof in an amount of from about 0.01 weight % to about 3 weight %, about 1 weight % to about 2 weight %, about 1.25 weight % to about 1.75 weight %, about 1.5 weight %, about 1 weight %, or about 0.5 weight %, based on a total weight of the oral care composition.

In at least one implementation, a weight ratio (e.g., weight %) of one surfactant to another surfactant may vary from about 0.5:1 to about 9:1. For example, the weight ratio of any one surfactant to another surfactant in the oral care composition may be from about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7:1, about 1.8:1, about 1.9:1, or about 2:1 to about 2.1:1, about 2.2:1, about 2.3:1, about 2.4:1, about 2.5:1, about 2.6:1, about 2.7:1, about 2.8:1, about 2.9:1, about 3:1, about 5:1, about 8:1, or about 9:1. In an exemplary implementation the weight ratio of at least one surfactant to another surfactant may be from about 0.5:1 to about 9:1, about 0.5:1 to about 3:1, about 1.5:1 to about 2.5:1, about 1.8:1 to about 2.2:1, or about 2:1.

In a preferred implementation, the oral care composition includes a combination of at least two surfactants. In at least one example, the at least two surfactants may include an anionic surfactant and a nonionic surfactant. In another example, the at least two surfactants may include an amino acid surfactant and a nonionic surfactant. The anionic surfactant may be or include, but is not limited to, a C6-C18 fatty acid glutamate salt or amino acid surfactants, such as a cocoyl glutamate salt, particularly sodium cocoyl glutamate. The nonionic surfactant may be or include, but is not limited to, one or more alkyl polyglucosides, such as one or more C6-C18 alkyl polyglucosides. In a preferred implementation, the oral care composition includes a C6-C18 fatty acid glutamate salt, such as sodium cocoyl glutamate, and a C8-C10 alkyl polyglucoside. The weight ratio (e.g., weight %) of the C8-C10 alkyl polyglucoside to the C6-C18 fatty acid glutamate salt may be from about 0.25:1 to about 9:1, about 1.5:1 to about 2.5:1, about 1.8:1 to about 2.2:1, or about 2:1.

Fluoride Ion Source

In at least one implementation, the oral care composition may be free or substantially free of fluoride (e.g., soluble fluoride salts). In another implementation, the oral care composition may include fluoride, such as one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium monofluorophosphate. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to provide a total of about 100 to about 20,000 ppm, about 200 to about 5,000 ppm, or about 500 to about 2,500 ppm fluoride ions.

Orally Acceptable Vehicle Or Carrier

The oral care composition may form at least a portion of or be used in one or more oral care products. The oral care composition may include or be combined with an orally acceptable vehicle. For example, the oral care composition may include or be combined with an orally acceptable vehicle to form the oral care product. The orally acceptable vehicle may include any known ingredients or additives. The orally acceptable vehicle may include various dentifrice ingredients to adjust the rheology and feel of the oral care composition.

In at least one implementation, the orally acceptable vehicle may include one or more humectants. Illustrative humectants may be or include, but are not limited to, glycerin, propylene glycol, polyethylene glycol, sorbitol, xylitol, or the like, or any mixture or combination thereof. In a preferred implementation, the orally acceptable vehicle may be or include, but is not limited to, sorbitol. The one or more humectants may be present in the oral care composition in an amount of from about 5 weight % to about 35 weight %, based on a total weight of the oral care composition.

In at least one implementation, the orally acceptable vehicle may include an orally acceptable solvent. Illustrative solvents may include, but are not limited to, one or more of ethanol, phenoxyethanol, isopropanol, water, cyclohexane, methyl glycol acetate, benzyl alcohol, or the like, or any mixture or combination thereof. In a preferred implementation, the orally acceptable solvent includes benzyl alcohol.

The orally acceptable vehicle may be present in an amount of from 5 weight % to about 60 weight %, based on a total weight of the oral care composition. For example, the orally acceptable vehicle may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %. In another example, the orally acceptable vehicle may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %. In an exemplary implementation, the orally acceptable vehicle may be present in an amount of about 20 weight % to about 30 weight %, preferably about 20 weight % to about 25 weight %, and more preferably about 22 weight % to about 25 weight %. In a preferred implementation, the orally acceptable vehicle may be present in an amount of about 22 weight % to about 25 weight % or about 23 weight %.

Thickening System and/or Viscosity Control Agents

The oral care product or the oral care composition thereof may include a thickening system having one or more thickeners. The one or more thickeners may be any orally acceptable thickener or thickening agent configured to control the viscosity of the oral care product or the oral care composition thereof. Illustrative thickeners may be or include, but are not limited to, colloidal silica, fumed silica, a cross-linked polyvinylpyrrolidone (PVP) polymer, cross-linked polyvinylpyrrolidone (PVP), or the like, or mixtures or combinations thereof. In at least one implementation, the thickening system includes a cross-linked polyvinylpyrrolidone (PVP) polymer. The thickening system may also include POLYPLASDONE® XL 10F, which is commercially available from Ashland Inc. of Covington, Ky. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBO-WAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof.

In a more typical implementation, the thickening system may include an organic polymer, which may also be configured as an adhesion enhancing agent. Illustrative organic polymers may be or include, but are not limited to, hydrophilic polymers, such as carbomers, such as carboxymethylene polymers, such as acrylic acid polymers, and acrylic acid copolymers. Carboxypolymethylene is a slightly acidic vinyl polymer with active carboxyl groups. In a typical embodiment, the thickening system includes a carboxypolymethylene, such as CARBOPOL® 974 and/or 980, which are commercially available from Noveon, Inc. of Cleveland, Ohio.

In at least one implementation, the thickening system may include a single thickener. For example, the thickening system may include the cross-linked polyvinylpyrrolidone (PVP) polymer or an organic polymer (e.g., CARBOPOL®). In another implementation, the thickening system may include a plurality of thickeners. For example, the thickening system may include the cross-linked PVP polymer and the organic polymer.

The amount or concentration of the thickening system and/or the thickeners thereof present in the oral care composition may vary widely. The amount of the thickening system and/or the thickeners thereof present in the oral care composition may from about 1.0 weight % to about 3.0 weight % based on the total weight of the oral care composition. For example, the amount of the thickening system and/or the thickeners thereof present in the oral care composition may be from about 1 weight %, about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, about 2.0 weight %, or about 2.1 weight % to about 2.2 weight %, about 2.3 weight %, about 2.4 weight %, about 2.5 weight %, about 2.6 weight %, about 2.7 weight %, about 2.8 weight %, about 2.9 weight %, or about 3.0 weight %. In another example, the amount of the thickening system and/or the thickeners thereof present in the oral care composition may from about 1.2 weight % to about 3.0 weight %, about 1.3 weight % to about 2.9 weight %, about 1.4 weight % to about 2.8 weight %, about 1.5 weight % to about 2.7 weight %, about 1.6 weight % to about 2.6 weight %, about 1.7 weight % to about 2.5 weight %, about 1.8 weight % to about 2.4 weight %, about 1.9 weight % to about 2.3 weight %, or about 2.0 weight % to about 2.2 weight %. In a typical implementation, the amount of the thickening system and/or the thickeners thereof present in the oral care composition may be from about 1.0 weight % to about 2.0 weight %, more typically about 1.2 weight % to about 1.8 weight %, and more typically about 1.5 weight %.

pH Modifying Agents

The oral care product or the oral care composition or a component thereof may include one or more pH modifying agents. For example, the oral care composition may include one or more acidifying agents and/or one or more basifying agents configured to reduce and/or increase the pH thereof, respectively. Illustrative acidifying agents and/or one or more basifying agents may be or include, but are not limited to, an alkali metal hydroxide, such as sodium hydroxide and/or potassium hydroxide, citric acid, hydrochloric acid, or the like, or combinations thereof.

The oral care composition or a component thereof may also include one or more buffering agents configured to control or modulate the pH within a predetermined or desired range. Illustrative buffering agents may include, but are not limited to, sodium bicarbonate, sodium phosphate, sodium carbonate, sodium acid pyrophosphate, sodium citrates and mixtures thereof. Sodium phosphate may include monosodium phosphate ($NaH_2PO_4$), disodium phosphate ($Na_2HPO_4$), trisodium phosphate ($Na_3PO_4$), and mixtures thereof. In a typical implementation, the buffering agent may be anhydrous sodium phosphate dibasic or disodium phosphate and/or sodium phosphate monobasic. In another implementation, the buffering agent includes anhydrous sodium phosphate dibasic or disodium phosphate, and phosphoric acid (e.g., syrupy phosphoric acid; 85%-Food Grade).

In at least one implementation, the acidifying, buffering, and/or buffering agents may be included in the oral care composition or a component thereof to provide a generally neutral pH or an orally acceptable pH range. In another implementation, the acidifying, buffering, and/or buffering agents may be included in the oral care composition or a component thereof (e.g., hydrophobic and/or hydrophilic phases) with a pH between 2 to 10, 2 to 8, 3 to 9, 4 to 8, 6 to 10, or 7 to 9. Any additional orally acceptable pH modifying agent may be used, including without limitation carboxylic, phosphoric, and sulfonic acids, acid salts (e.g., monosodium citrate, disodium citrate, monosodium malate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc.), imidazole and mixtures thereof. The one or more pH modifying agents may be optionally present in an amount effective to maintain the oral care composition or a component thereof in an orally acceptable pH range.

Flavoring Agents

The oral care product and/or the oral care composition thereof may also include one or more flavoring agents. Illustrative flavoring agents may include, but are not limited to, essential oils and various flavoring aldehydes, esters, alcohols, or the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, carvone, and anethole. In a typical implementation, the flavoring agent includes peppermint and spearmint. In a more typical implementation, the flavoring agent includes a Firmenich Newman Flavor. The amount of the flavoring agent in the oral care product and/or the oral care composition thereof may be less than 1.0 wt %, less than 0.9 wt %, less than 0.8 wt %, or less than 0.7 wt %. For example, the amount of the flavoring agent in the oral care product and/or the oral care composition thereof may be about 0.0 wt % to about 1.0 wt %, about 0.5 wt % to about 0.9 wt %, about 0.7 wt % to about 0.8 wt %. In a typical implementation, the amount of the flavoring agent in the oral care product and/or the oral care composition thereof is about 0.55 wt % to about 0.70 wt %.

Additional Ingredients

It should be appreciated to one having ordinary skill in the art, that the oral care products and/or the oral care composition thereof may include other additional ingredients/components. For example, the oral care products and/or the oral care composition thereof may include any one or more of anti-caries agents, desensitizing agents, viscosity modifiers, diluents, pH modifying agents, humectants, mouth feel agents, sweetening agents, flavor agents, colorants, preservatives, or the like, or combinations and mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity, such as dentinal hypersensitivity. The active materials may also be configured to prevent and/or treat one or more physiological disorders and/or conditions, and/or provide a cosmetic benefit to the oral cavity.

In at least one implementation, the oral care products or the oral care composition thereof may include an anticalculus agent. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In a typical implementation, the anticalculus agent includes tetrasodium pyrophosphate (TSPP), sodium tripolyphosphate (STPP), or a combination thereof.

The oral care products or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations and mixtures thereof.

The oral care composition may include zinc. The zinc of the oral care composition may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc oxide, zinc phosphate, zinc picolinate, zinc proprionate, zinc salicylate, zinc silicate, zinc stearate, zinc tartrate, zinc undecylenate, and mixtures thereof. In a preferred embodiment, the zinc salt is zinc lactate.

The oral care composition may include one or more pigments, such as whitening pigments. In some implementations, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the teeth.

Methods

The present disclosure may provide methods for treating dentinal hypersensitivity and/or cleaning teeth in a human or animal subject with an oral care product and/or the oral care composition thereof. As used herein "animal subject" may include higher order non-human mammals such as canines, felines, and horses. The method may include contacting the oral care product and/or the oral care composition thereof with water. The method may also include contacting the surface of the teeth with the oral care product and/or the oral care composition thereof. Contacting the surface of the teeth with the oral care product and/or the oral care composition thereof may include disposing the oral care composition (e.g., toothpaste) on a toothbrush and brushing the teeth with the toothbrush.

The oral care product and/or the oral care composition thereof may be applied and/or contacted with the surfaces of the teeth at predetermined intervals. For example, a daily basis, at least once a day, twice a day, or more, for multiple days, or alternatively every other day. In another example, the oral care product and/or the whitening composition thereof may be applied and/or contacted with the surfaces of the teeth at least once a day, at least once every two days, at least once every three days, at least once every five days, at least once a week, at least once every two weeks, or at least once a month. The oral care product and/or the oral care composition thereof may be utilized for up to 2 weeks, up to 3 weeks, up to 4 weeks, up to 6 weeks, up to 8 weeks, or greater.

The present disclosure may also provide methods for preparing oral care compositions having increased foam generation as compared to conventional oral care compositions. The method may include combining or contacting an orally acceptable vehicle with at least two surfactants, including an anionic surfactant and a nonionic surfactant, where the anionic surfactant includes a C8-C16 fatty acid glutamate salt or amino acid surfactants, such as a cocoyl glutamate salt, particularly sodium cocoyl glutamate, and where the nonionic surfactant includes an alkyl polyglucosides, such as a C8-C16 alkyl polyglucoside. The method may further include combining the orally acceptable vehicle, the anionic surfactant, and the nonionic surfactant with one or more amino acids and one or more abrasives. For example, the method may include combining the orally acceptable vehicle, the anionic surfactant, and the nonionic surfactant with arginine or a source of arginine and calcium carbonate.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The efficacy of varying oral care compositions for producing foam was evaluated. Particularly, a control toothpaste composition (C) and five exemplary or test toothpaste compositions (1)-(5) were prepared by combining the ingredients/components of a base toothpaste composition indicated in Table 1, with the respective surfactant(s) indicated in Table 2. The components were mixed for about 10 minutes under mechanical stirring to prepare each of the toothpaste compositions (C) and (1)-(5).

TABLE 1

Base Toothpaste Composition

| INGREDIENT/COMPONENT | Concentration (Weight %) |
|---|---|
| Sorbitol - non-crystal - 70% solution | 23.0% |
| EP Purified water | 10.0% |
| Benzyl Alcohol | 0.7% |
| Arginine Bicarbonate solution 40.8% | 19.6% |
| Sodium Monofluorophosphate | 1.1% |
| Tetrasodium pyrophosphate | 0.5% |
| Sodium Bicarbonate | 0.5% |
| Precipitated calcium carbonate - Medium Absorption | 10.0% |
| Precipitated calcium carbonate - High Absorption | 25.0% |
| Zinc Oxide (ZnO) | 1.0% |
| Zinc Citrate | 0.5% |
| Titanium Dioxide (TiO$_2$) | 0.5% |
| Excipients | Balance |

TABLE 2

Surfactant(s) Added to Base Toothpaste Composition to Prepare Control Toothpaste Composition © and Exemplary Toothpaste Compositions (1)-(6)

| SURFACTANTS | (C) | (1) | (2) | (3) | (4) | (5) |
|---|---|---|---|---|---|---|
| 29% Sodium Lauryl Sulfate (SLS) (g) | 4.9 | — | — | — | — | — |
| 65% Alkyl Polyglucoside-08/10 (g) | — | 2.2 | — | 1.5 | 0.7 | — |
| 50% Alkyl Polyglucoside-12/14 (g) | — | — | — | — | — | 2.8 |
| 43% Sodium Cocyl Glutamate (g) | — | — | 3.3 | 1.1 | 2.2 | — |
| Total Concentration of Surfactants (weight %) | 1.5 | 1.5 | 1.5 | 1.5 | 1.5 | 1.5 |

To evaluate the efficacy for producing foam, a Krüss Dynamic Foam Analyzer (DFA100), commercially available from Krüss GmbH of Hamburg, Germany, was utilized. The Krüss Dynamic Foam Analyzer was adjusted according to the parameters/testing conditions indicated in Table 3.

TABLE 3

Parameters of Krüss Dynamic Foam Analyzer

| PARAMETER | TESTING CONDITION |
|---|---|
| Sample Concentration | 30% |
| Stirring Speed | 5,000 RPM |
| Oscillation Intervals | 6 sec |
| Foam Time | 60 sec |
| Delay Time | 450 sec |

The results of the foam generation are summarized in Table 4.

TABLE 4

Summary of Foam Generation in Control Toothpaste Composition (C) and Exemplary Toothpaste Compositions (1)-(6)

| Sample | Active Foaming Agent | Maximum Foam Volume (mL) |
|---|---|---|
| (C) | 1.5% Sodium Lauryl Sulfate (SLS) | 86.1 |
| (1) | 1.5% Alkyl Polyglucoside C8-C10 | 111.2 |
| (2) | 1.5% Sodium Cocoyl Glutamate | 107.0 |
| (3) | 1% Alkyl Polyglucoside C8-C10 + 0.5% Sodium Cocoyl Glutamate | 125.4 |
| (4) | 0.5% Alkyl Polyglucoside C8-C10 + 1% Sodium Cocoyl Glutamate | 117.0 |
| (5) | 1.5% Alkyl Polyglucoside C12-C14 | 72.6 |

As indicated in Table 4, the combination of the glutamate surfactant, particularly, sodium cocoyl glutamate, and the alkyl polyglucoside surfactant surprisingly and unexpectedly exhibited synergistic or more than additive foaming as compared to each of the surfactants alone. Without being bound by theory, it is believed that the nonionic structure of the glucoside surfactant and the negatively charged structure of the glutamate surfactant may contribute to the synergistic results. Particularly, it is believed that the nonionic structure of the glucoside surfactant and the negatively charged structure of the glutamate surfactant prevents interactions therebetween, thereby increasing the foaming in the toothpaste formulation.

As also indicated in Table 4, providing relatively greater amounts of the nonionic polyglucoside surfactant to the anionic glutamate surfactant, as represented by test toothpaste compositions (3), surprisingly and unexpectedly produced more foam as compared test toothpaste compositions (4), which included relatively greater amounts of the anionic glutamate surfactant. Accordingly, it was surprisingly and unexpectedly discovered that increased amounts or ratios of the nonionic surfactant relative to the anionic surfactant provides improved foaming.

As further indicated in Table 4, short carbon chain polyglucosides, as represented by test toothpaste composition (1) produced relatively increased amounts of foam as compared to toothpaste compositions (5), which included longer carbon chain polyglucosides, and the control toothpaste composition (C), which included SLS alone.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care composition, comprising:
   an orally acceptable vehicle;
   an anionic surfactant comprising a sodium cocoyl glutamate or a salt thereof; and
   a nonionic surfactant comprising a C8-C10 alkyl polyglucoside, wherein the weight ratio of the nonionic surfactant to the anionic surfactant is from 2:1 or 1:2.

2. The oral care composition of claim 1, further comprising an amino acid.

3. The oral care composition of claim 2, wherein the amino acid comprises one or more of arginine, lysine, citrulline, ornithine, creatine, histidine, diaminobutanoic acid, diaminoproprionic acid, salts thereof, or combinations thereof.

4. The oral care composition of claim 2, wherein the amino acid comprises arginine, optionally, the arginine is provided by arginine bicarbonate, further optionally, the arginine is provided by an arginine bicarbonate solution.

5. The oral care composition of claim 1, further comprising an abrasive.

6. The oral care composition of claim 5, wherein the abrasive comprises one or more of sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, calcium carbonate, magnesium carbonate, hydrated alumina, silica, zirconium silicate, aluminum silicate, calcined aluminum silicate, polymethyl methacrylate, or combinations thereof.

7. The oral care composition of claim 5, wherein the abrasive comprises calcium carbonate, optionally, the calcium carbonate comprises natural calcium carbonate or precipitated calcium carbonate.

8. The oral care composition of claim 1, wherein the oral care composition is substantially free of alkyl sulfate salts, optionally the alkyl sulfate salts comprises sodium lauryl sulfate.

9. The oral care composition of claim 1, wherein the oral care composition is a toothpaste.

10. A method for preparing the oral care composition of claim 1, comprising contacting the orally acceptable vehicle, the anionic surfactant, and the nonionic surfactant with one another.

11. A method for treating dentinal hypersensitivity in a human, the method comprising contacting the oral care composition of claim 1 with surfaces of teeth of the human.

12. The method of claim 11, further comprising contacting the oral care composition with surfaces of the teeth of the human at least once a day, optionally, twice a day.

13. The oral care composition of claim 1, wherein the weight ratio of the nonionic surfactant to the anionic surfactant is from 2:1.

14. The oral care composition of claim 1, wherein a weight ratio of the nonionic surfactant to the anionic surfactant is from 1:2.

15. The oral care composition of claim 1, wherein the nonionic surfactant and anionic surfactant are present in a combined amount of about 1.5% by wt of the total composition.

16. The oral care composition of claim 1, wherein the nonionic surfactant is present in an amount of about 0.5%, or about 1%, by wt. of the total composition.

17. The oral care composition of claim 1, wherein the anionic surfactant is present in an amount of in an amount of about 0.5%, or about 1%, by wt. of the total composition.

* * * * *